United States Patent [19]

Harmer

[11] Patent Number: 4,641,965
[45] Date of Patent: Feb. 10, 1987

[54] IMMERSION REFRACTOMETER WITH ANGLE PRISM

[75] Inventor: Alan L. Harmer, Plan Les Ouates, Switzerland

[73] Assignee: Stanley Electric Co. Ltd., Tokyo, Japan

[21] Appl. No.: 648,795

[22] Filed: Sep. 7, 1984

[30] Foreign Application Priority Data

Sep. 7, 1983 [CH] Switzerland ......................... 4883/83

[51] Int. Cl.$^4$ ........................................... G01N 21/41
[52] U.S. Cl. .................................. 356/135; 356/128; 356/133
[58] Field of Search ................ 356/135, 133, 128, 130

[56] References Cited

U.S. PATENT DOCUMENTS 3,426,211 2/1969 Anderson ............................. 356/135
3,674,373 2/1970 Waters et al. ....................... 356/130

FOREIGN PATENT DOCUMENTS 1529518 6/1968 France .

Primary Examiner—R. A. Rosenberger
Assistant Examiner—Crystal D. Cooper
Attorney, Agent, or Firm—Karl F. Ross; Herbert Dubno

[57] ABSTRACT

A refractometer comprises a light source, an angle prism and an optical system in a casing so mounted that the optical system focuses an image of a diaphragm at said light source upon a double photodiode located beyond the prism and supported by an oblique surface of the casing. The ratio of the output of one photodiode to the output of the double photodiode is measured to register the index of refraction.

8 Claims, 3 Drawing Figures

IMMERSION REFRACTOMETER WITH ANGLE PRISM

FIELD OF THE INVENTION

The present invention relates to an immersion refractometer provided with a prism and, more particularly, to a refractometer of the type which comprises a tube provided with a prism which is intended to be partially immersed in a liquid.

BACKGROUND OF THE INVENTION

There are two major categories of refractometers, namely, those based upon variation in the intensity of an incident beam, ray or pencil of radiation (light) and those based upon the refraction of a pencil of such radiation in the region of the critical angle.

Refractometers based upon intensity variation are sensitive to the intensity of the luminous sources and the transparency of the liquid. Refractometers operating by refraction at the critical angle provide a signal which is not quite clean.

It has been proposed to provide a refractometer which comprises at least two photosensitive detectors for determining which permits a determination to be made of the index of refraction of a liquid by measuring the ratio of the luminous intensities received by the two detectors. Such refractometers have been described in U.S. Pat. No. 3,674,373 and in French Pat. No. 1,529,518. The refractometer of the latter can be used as a laboratory apparatus for the analysis of samples but is not in the form of a simple apparatus capable of more general use or more versatile application by simply being introduced into a receptacle containing the liquid whose index of refraction is to be measured.

A simple apparatus of this type is required, for example, to measure the index of refraction of a liquid in the measurement of the state of charge of an electric storage battery or in the production of such batteries or any production process in which a simple and rapid measurement locally and in place of the refractive index of a liquid is desired.

OBJECTS OF THE INVENTION

It is the principal object of the present invention to provide a simple refractometer which can be utilized by itself simply by immersion into a vessel containing the liquid to be evaluated but which can also, if desired, be incorporated into practically any apparatus requiring a measurement of the index of refraction of the liquid.

Another object of this invention is to provide an improved apparatus for measuring the refractive index which is of simple and inexpensive construction and which is easy to use.

Still another object of the invention is to provide an easily handled device for measuring refractive index which avoids drawbacks of earlier devices.

Yet another object of the invention is to provide a refractometer which is particularly suitable for measurement of the index of refraction in production processes and the refractive index of a battery electrolyte in situ.

SUMMARY OF THE INVENTION

These objects and others which will become apparent hereinafter are attained, in accordance with the invention in a refractometer which comprises a tubular casing formed at one end with a prism adapted to be partly immersed in a liquid and provided, at a location spaced from this prism, with a light source, means for measuring the variation of the angle of refraction of light as a function of the index of refraction of the liquid, a diaphragm in the path of a pencil of light emitted by this source having an orifice and forming a collimator for passing only an extremely narrow pencil or ray, and an optical system, i.e. a lens system, in the path of the pencil of light traversing this diaphragm for forming an image of the diaphragm orifice. The prism is disposed in the path of the pencil of light traversing the optics and has a face exposed to the atmosphere and turned toward the optics, the pencil of light emerging from the prism at a face of the latter located below the liquid level.

According to the invention, the measuring means comprises a double photodiode whose junction is located in a focal plane of the optics and substantially along the axis of refraction of the pencil for a given index of refraction of the liquid. The index of refraction can thus be measured as a function of the ratio between the signal outputted from one of these photodiodes and the sum of the signals outputted by the double photodiode. The prism, the light source, the diaphragm, the optics and the double photodiode are mounted on a tubular casing whose longitudinal axis coincides with the optical axis of the elements named.

The refractometer of this invention thus measures the actual angle of refraction in terms of the aforementioned ratio and the output signal is extremely clean since the image of the orifice is focused on the double photodiode and any movement of the focal point resulting from a change in the angle of refraction will provide a clear change in the ratio of the intensity of illumination received from one of the two photodiodes and the sum of the intensities of the two photodiodes of the double photodiodes.

The evaluation circuitry need only determine the ratio to provide an output signal which can be calibrated in index of refraction. The measurement is independent of the intensity of the source and of the transparency of the liquid.

Another advantage of the refractometer of the invention is the simplicity of the apparatus and the comparatively small number of elements or components used therein.

Indeed, tests have shown that the apparatus is highly reliable and precise, at least in part because all of the elements of the refractometer are in position upon manufacture and no adjustment or resetting is required for use or calibration.

BRIEF DESCRIPTION OF THE DRAWING

The above and other objects, features and advantages of the present invention will become more readily apparent from the following description, reference being made to the accompanying drawing in which.

SPECIFIC DESCRIPTION

Figure 1:
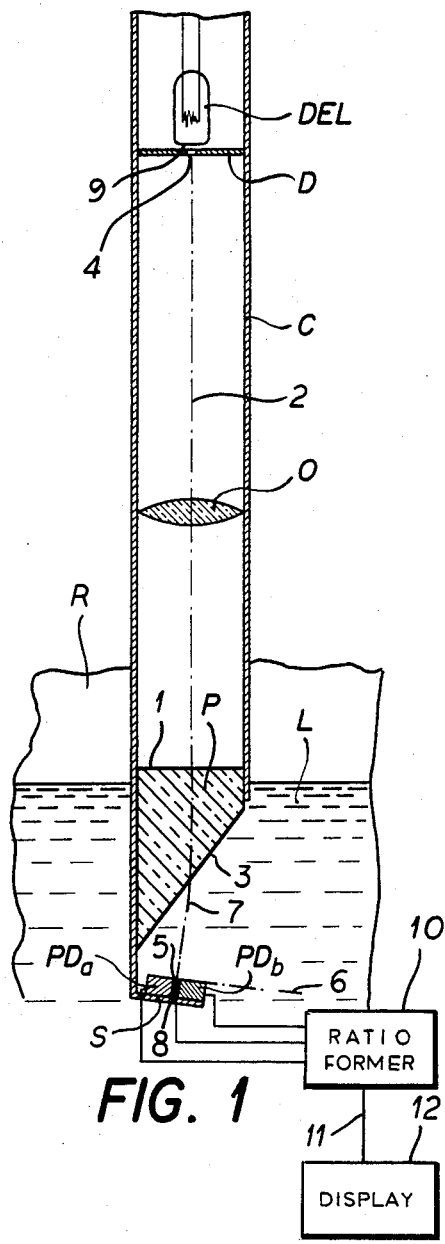
FIG. 1 is a vertical section through a refractometer according to the invention.

The refractometer shown in FIG. 1 comprises a tubular casing C which is cut at a bias at its lower end to receive a prism P which is partly immersed in a liquid L in a respective wall of which has been represented at R.

The prism P has an upper surface 1 exposed to the atmosphere and out of the liquid L, this surface being perpendicular to a pencil 2 of light which traverses the prism P and emerges at the immersed face 3 of the prism which lies at an angle to the surface 1 and to the axis of the ray 2.

The liquid L can be any liquid whose index of refraction is to be measured and particularly a liquid whose concentration can be measured as a function of index of refraction, such as alcohol in the production of alcohol of alcoholic beverages, of an acid in an electric storage battery electrolyte.

The source of light consists of an electroluminiscent diode DEL located above the upper face of the prism and energized by an electric current source not shown but which may have batteries built into the case above the light source.

A diaphragm D is located immediately below the light source and has an orifice 4 which serves to collimate the pencil of light 2 and provide a luminous spot an image of which can be focused at a point 5 by an optical system represented by the lens O which may be a fixed focus system. The diaphragm D, therefore, is thus provided between the light source and the optical system. The optical system can comprise a plurality of lenses and is intended to focus the light in the plane 6 below the prism and in the liquid.

A double photodiode $PD_a$ and $PD_b$ is located in this focal plane 6 and is fixed in place on a support tongue formed by a bent portions of the lower end of the case which is truncated oblique angle to the longitudinal axis thereof.

This angle is perpendicular to the portion 7 of the beam which is refracted by the exit face 3 of the prism P in contact with the liquid L.

The junction 8 between the two photodiodes is located at the focused image, i.e. along the optical axis of the image of diaphragm D for a given index of refraction of the liquid so that for the latter index of refraction the signals to the two photodiodes are equal.

When the index of refraction of the liquid increases, the refracted beam is displaced to the right and the signal from photodiode $PD_b$ increases while that of the photodiode $PD_a$ is reduced.

In order to have a good ratio and hence contrast between the current of the photodiode $PD_a$ and the total current it is necessary that the image of the diaphragm D on the double photodiode $PD_a$, $PD_b$ also being as clean as possible and that a maximum capture of light is effected.

Tests have shown that the dimension of the image of the diaphragm in the direction transverse to that of its displacement should be of the order of 0.10 millimeters. The corresponding dimension of the diaphragm was then selected to be 0.060 millimeters to provide a maximum passage of the illumination from the electroluminiscent diode DEL which does not act as a point source.

The end face 9 of the diode can be cut and polished and it can then be cemented to the diaphragm and thereby mounted in the casing.

Tests of the variation of current intensitiy of the double photodiode $PD_a$, $PD_b$ as a function of its displacement in the plane 6 and thus of the relative displacement of the double photodiode to the focal point, were made under the following conditions. The electroluminiscent diode DEL was of the Stanley type ESBR 5501 and was cemented to a diaphragm having a rectangular opening of a width of 0.60 millimeters.

Figure 2:
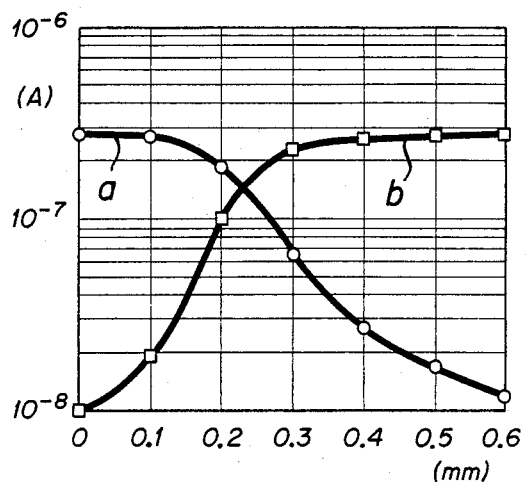
FIG. 2 is a graph in which the luminous intensity of an image of a light spot on the two photodiodes of the device of FIG. 1 is plotted as a function of the relative displacement of this light spot and the photodiodes.

The optical lens, was a 6 millimeter diameter, f/10 mm lens and the double photodiode $PD_a$ $PD_b$ was spaced from it by a distance of 40 millimeters upon a micrometric slide table (optical table). FIG. 2 in curves a and b shows the variation of the current intensity of the photodiode $PD_a$ and the photodiode $PD_b$, respectively. Along the ordinate these current intensities have been plotted in a logarithmic scale as a function of the displacement plotted along the abscissa.

In this diagram the displacement corresponding to 10% of the maximum intensity of the curves a and b is equal to 0.27 millimeters.

The displacement between two points of intensity corresponding to 10% of the maximum intensity can be considered to correspond to the width of the image of the diaphragm formed on the double photodiode.

When the diodes are separated by 0.05 millimeters from one another (junction width=0.05 mm), the points corresponding to 10% of maximum intensity represent a displacement of 0.27 millimeters when the image of the diaphragm has a width of 0.32 millimeters. The assembly of the diaphragm D, the optics and the double photodiodes in effect represents a multiplier which multiplies the image by 2.7 times such that the nonmultiplied image has a width of 0.12 millimeters, corresponding to the dimensions which given a good contrast between the current of the photodiode $PD_a$ and the total current of the double photodiode $PD_a$ and $PD_b$.

In the refractometer illustrated in FIG. 1, the prism P is composed of a polymethylmethacrylate (Plexiglas). The inclination of the oblique faces, selected for the source and the liquid, is such that the angle of incidence upon it is 52.5 degrees. The light then enters the liquid 1 at an angle of refraction of 60° for a mean index of refraction of the liquid to be measured.

The plane of the double photodiode is located 4 millimeters from the point at which the liquid beam emerges from the prism.

The deflection of the beams as a function of the index of refraction of the liquid is easily calculated.

For example, for a lead acid battery electrolyte which contains sulfuric acid at a concentration of 15–40% the index of refraction varies from $n=1.35$ to $n=1.38$ and the index of refraction at which the beam is apportioned equally between the photodiodes is 1.3680.

The angle of refraction varies from $\sin^{-1}(1.49/1.35 \sin 52.5°)=61.12°$ to $\sin^{-1}(1.49/1.38 \sin 52.5°)=58.94°$.

The linear displacement of the beam is equal to $4.0 \sin(61.12-58.94)=0.152$ millimeters.

Figure 3:
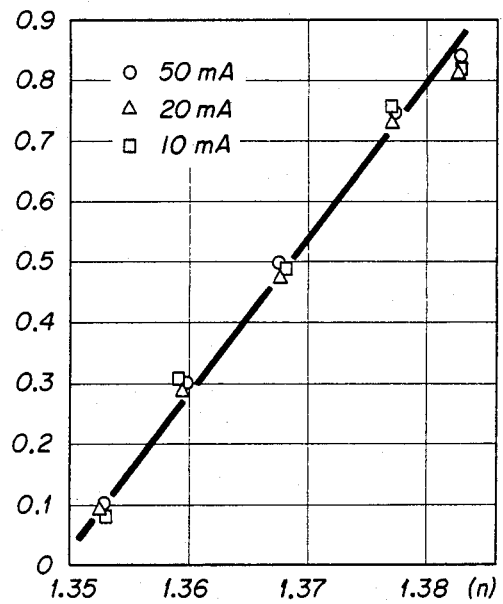
FIG. 3 is a graph plotting the ratio of the intensity of one photodiode to the total intensity along the ordinate against the refractive index of the liquid, plotted along the abscissa.

As can be seen from FIG. 3, over the entire range of the displacement and within the critical range of refractive indeces, the ratio between the output of the photodiode $PD_a$ and the output of the double photodiode $PD_a$ $PD_b$ is absolutely linear.

If any nonlinearity enters into the result it is due to the fact that the beams of measurement may be close to the actual boundaries of the double photodiode. When the displacement of the image is such that it reaches the limits of the photodiode, current intensity will no longer reflect displacement of the image.

The f/10 millimeter lens of the optical system O is placed at a distance 2f or 20 millimeters from the diaphragm and from the surface of the double photodiode, thereby theoretically generating an image of the orifice of the diaphragm upon the photodiode of the same dimensions. However, since the light source is in a point source, there is a certain amount of dispersion which explains the fact that the image on the photodiode is about twice the width of 0.06 millimeters of the orifice.

The diagram of FIG. 2 also shows that the results are practically independent of source intensity since measurements with sources energized at 10 mA, 20 mA and 50 mA have been plotted.

A ratio forming circuit 10 is connected on the one hand to the photodiode $PD_a$ and on the other hand across the double photodiode $PD_a PD_b$ to form the ratio of outputs plotted along the ordinate in FIG. 3 and generates a corresponding output signal at 11 which can be fed to a display 12 calibrated directly in terms of refractive index for the particular liquid. The circuits 11 and 12 can be housed in the casing also.

I claim:

1. A refractometer comprising:
   a tubular casing;
   a prism disposed at one end of said casing and adapted to be immersed partially in a liquid whose index of refraction is to be measured;
   a light source in said casing spaced from said prism;
   a diaphragm in said casing between said light source and said prism and having an orifice passing a pencil of light;
   lens means in the path of said pencil of light in said casing between said diaphragm and said prism for focusing an image of said orifice in a plane beyond said prism in said liquid; and
   a double photodiode adapted to be immersed in said liquid having two coplanar discrete photodiodes forming a junction located in said plane substantially along an axis of refraction of said pencil for a given index of refraction of said liquid, said double photodiode having an output detected across both said discrete photodiodes, means being provided to establish a ratio between an output intensity of one of said discrete photodiodes and the intensity of said output of said double photodiode as a measure of the index of refraction of said liquid.

2. The refractometer defined in claim 1 wherein said end of said casing is formed with a support at an angle oblique to said axis and carrying said double photodiode.

3. The refractometer defined in claim 1 wherein said prism is sealed and fixedly positioned in said casing and prevents passage of said liquid into said casing.

4. The refractometer defined in claim 2 wherein said prism has a surface perpendicular to said axis in said casing exposed to the atmosphere and a surface inclined to said axis exposed to said liquid.

5. The refractometer defined in claim 4 wherein said light source is an electroluminescent diode.

6. The refractometer defined in claim 5 wherein said lens means includes a lens disposed substantially equidistant between said double photodiode and said diaphragm.

7. The refractometer defined in claim 6 wherein said source is cemented to said diaphragm.

8. The refractometer defined in claim 7 further comprising ratio forming circuitry connected to said one of said photodiodes and said double photodiode for forming an output signal representing refractive index.

* * * * *